United States Patent [19]

Moldt

[11] Patent Number: 5,166,441
[45] Date of Patent: Nov. 24, 1992

[54] ASTAXANTHIN INTERMEDIATES

[75] Inventor: Peter Moldt, Humlebaek, Denmark

[73] Assignee: NeuroSearch A/S, Glostrup, Denmark

[21] Appl. No.: 805,997

[22] Filed: Dec. 9, 1991

Related U.S. Application Data

[62] Division of Ser. No. 626,573, Dec. 12, 1990, Pat. No. 5,107,010.

[51] Int. Cl.$^5$ .................................... C07C 317/26
[52] U.S. Cl. .................................... 564/440; 568/30; 568/31; 568/33
[58] Field of Search .................... 568/30, 31, 33; 564/440

[56] References Cited

U.S. PATENT DOCUMENTS

| | | | |
|---|---|---|---|
| 4,384,143 | 5/1983 | Fox et al. | 568/33 |
| 4,469,891 | 9/1984 | Fayter et al. | 568/31 |
| 4,777,297 | 10/1988 | Ogawa et al. | 568/33 |
| 4,822,905 | 4/1989 | Lee et al. | 568/31 X |
| 4,837,352 | 6/1989 | Knudsen | 568/30 X |
| 4,867,784 | 9/1989 | Keil et al. | 568/31 X |
| 4,960,940 | 10/1990 | Papenfuhs et al. | 564/440 |
| 5,110,343 | 5/1992 | Ueda et al. | 568/30 X |

Primary Examiner—Paul F. Shaver
Attorney, Agent, or Firm—Gordon W. Hueschen

[57] ABSTRACT

The present invention related to novel compounds useful in the manufacture of astaxanthin and to processes for their preparation. The novel intermediates have the formula

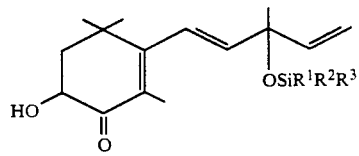

wherein $R^1$, $R^2$ and $R^3$ independently are $C_{1-6}$-alkyl which may be branched or phenyl, and

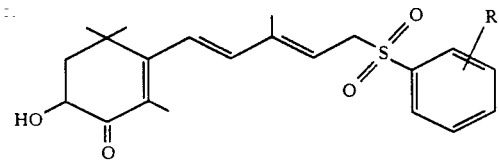

wherein R' is alkyl, alkoxy, $NO_2$, $NH_2$ or halogen.

2 Claims, No Drawings

ASTAXANTHIN INTERMEDIATES

This application is a division of may prior-filed copending U.S. application Ser. No. 07/626,573, filed Dec. 12, 1990, now U.S. Pat No. 5,107010.

FIELD OF INVENTION

The present invention relates to a novel process for the manufacture of novel intermediates useful in the manufacture of astaxanthin. Furthermore the present invention relates to a novel process for the manufacture of astaxanthin utilizing said intermediates.

OBJECTS OF THE INVENTION

It is an object of the present invention to provide novel key compound's for the manufacture of astaxanthin, as well as novel processes for the production of the same.

BACKGROUND OF THE INVENTION

The closest background art of the invention is disclosed in U.S. Pat. No. 4,585,885 in which a compound having the formula

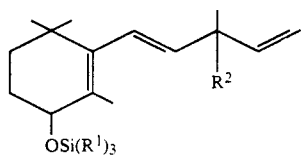

wherein $R^3$ is an trialkylsiloxy group or an ether group, is oxidized with a percarboxylic acid to form a compound having the formula

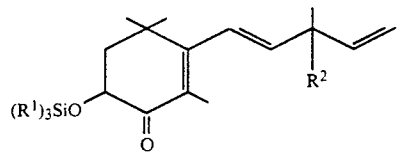

wherein $R^2$ is as above.

This compound is then transformed into a compound having the formula

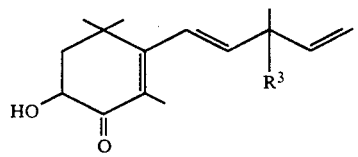

wherein $R^3$ is an alkylether or an hydroxy group.

This compound is then transformed into a Wittig compound which upon reaction with a compound having the formula

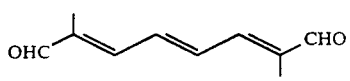

will yield astaxanthin.

DETAILED DESCRIPTION

The novel process of the present invention is carried out much more convenient, in that it avoids the use of peracids and allows a much more direct approach to the production of astaxanthin.

The novel process and the novel intermediates of the invention is illustrated in below scheme

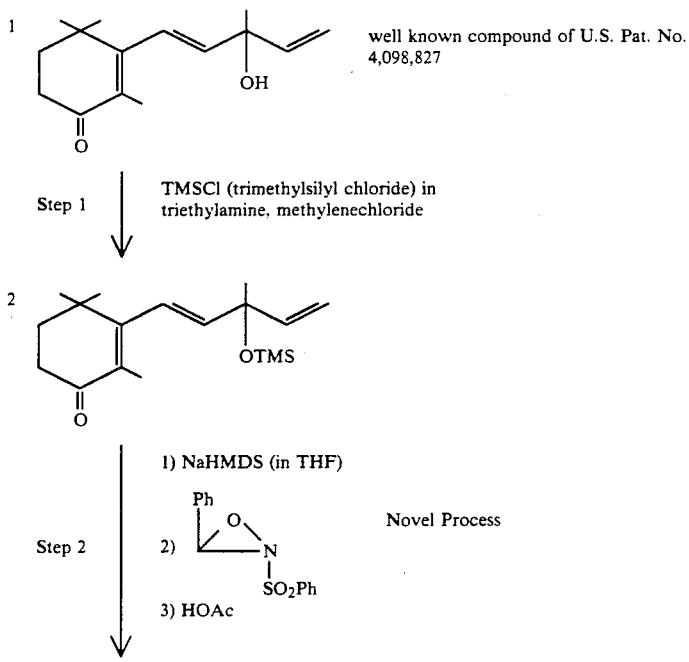

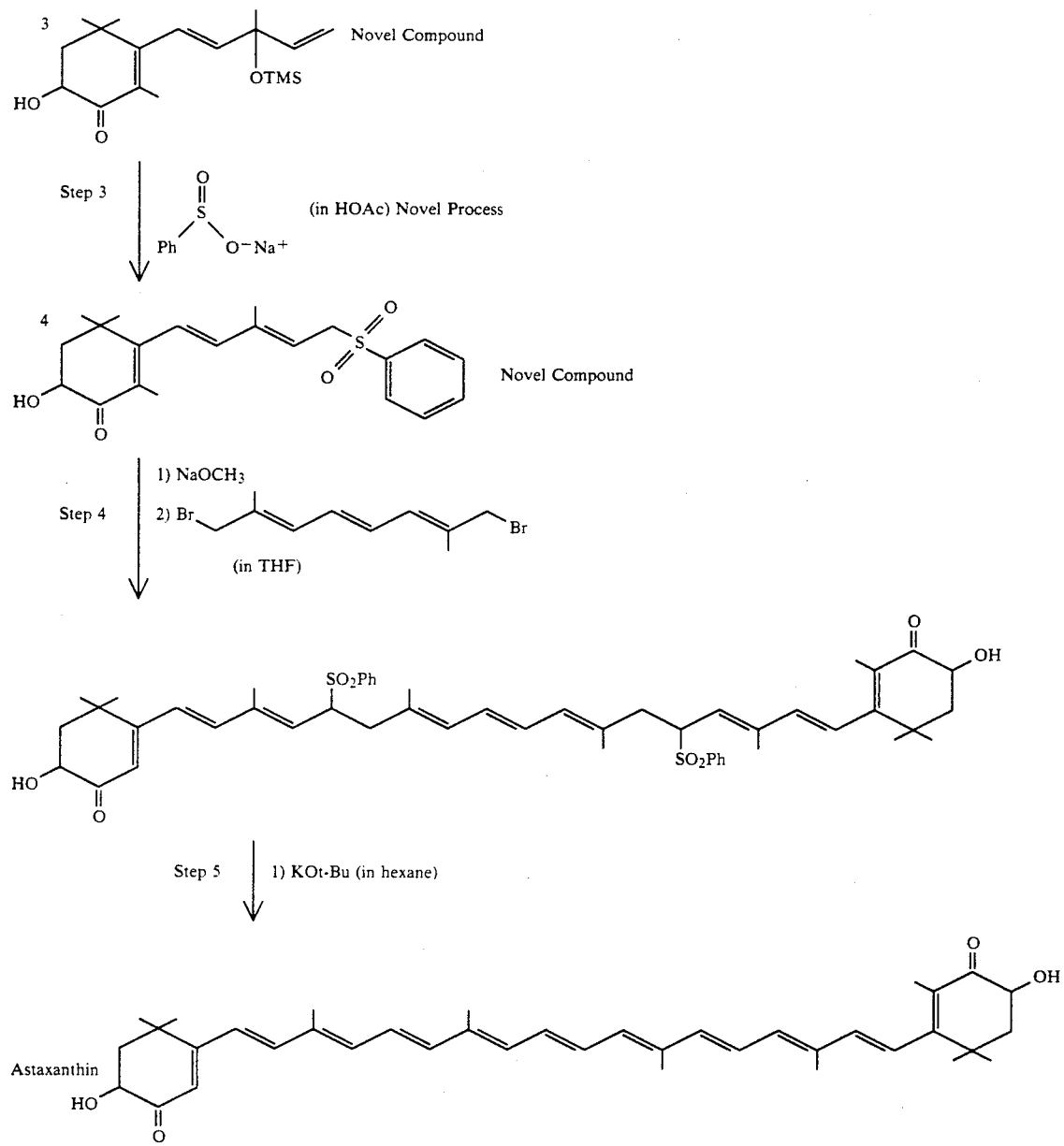

The above scheme illustrate preferred reagents, solvents, acids and bases of the processes of the invention.

However the NaHMDS (sodiumhexamethyldisilazane) of step 2 above may easily be substituted for other bases as for example KHMDS, LiHMDS, LDA (lithium diisopropyl amide), sodiumhydride, potassium t-butylat as well as several others.

The oxidizing agent of step 2, trans-2-(phenylsulfonyl)-3-phenyloxaziridine

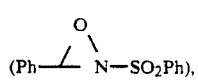

is a key element of step 2. However, this oxidizing agent may be any oxaziridine having the below formula

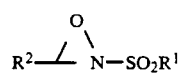

wherein $R^1$ is phenyl, phenyl substituted with a substituent which is stable under the conditions of reaction, $C_{3-7}$-cycloalkyl, and wherein $R^2$ independently signifies hydrogen or the same radical as $R^1$, or wherein $R^1$ and $R^2$ together form a cyclic or bicyclic radical as for example camphorylsulfonyloxaziridine.

The acid of step 2 used to quench the reaction mixture may be any proton donor. Any protic compounds such as water, alcohols, and hydrogen-donating acids may be employed, however, it preferred that the quenching proton donor is at least slightly acidic in order to avoid the formation of strong base during the quenching step.

The phenylsulphinate employed in step 3 above may be substituted for any substituted derivative thereof. For example the phenyl group may be substituted with alkyl, alkoxy, NO₂, and halogen. The acetic acid employed in this step 3 may be substituted by any organic acid, or any neutral organic solvent with addition of an acid, for example ethanol added hydrogen chloride may conveniently be employed instead.

Step 4 and 5 above illustrate the utility of the novel intermediates of the invention produced by the novel processes of the invention for the production os astaxanthin.

Step 4 and step 5 above may conveniently be effected by use of the reagents indicated above. The principles of the processes are described in more detail in examples 5 and 6 of U.S. Pat No. 4,049,718.

EXAMPLES

The invention will now be described in greater detail with reference to the following examples, which are given by way of illustration only and are not to be construed as limiting.

1-(3-oxo-2,6,6-trimethyl-1-cyclohexen-1-yl)-3-methyl-3-trimethylsiloxy-1,4-pentadiene A solution of 1-(3-oxo-2,6,6-trimethyl-1-cyclohexen-1-yl)-3-methyl-1,4-pentadiene-3-ol (2.34 g, 10 mmoles)(-prepared as described in J. Org. Chem. 47, 2130-2134 (1982)) in methylenechloride is added triethylamine (2.08 ml, 15 mmoles), trimethylchlorosilane (1.9 ml, 15 mmoles), and N,N-dimethyl-4-aminopyridine (5 mg, catalytic amount). The mixture is stirred at room temperature for four hours, followed by concentration in vacuo and trituration with dry diethylether. The suspension is filtered and the filtrate is concentrated in vacuo yielding the title compound as a slightly yellow oil.

1-(4-hydroxy-3-oxo-2,6,6-trimethyl-1-cyclohexen-1-yl)-3-methyl-3-trimethylsiloxy-1,4-pentadiene A solution of 1-(3-oxo-2,6,6-trimethyl-1-cyclohexen-1-yl)-3-methyl-trimethylsiloxy-1,4-pentadiene (918 mg, 3 mmoles) in 10 ml absolute tetrahydrofurane at −20° C. is slowly added sodium hexamethyldisilazane (4.5 ml 1M in THF, 4.5 mmoles) forming a violet solution of sodium-enolate. The mixture is stirred 30 minutes at −20° C., the temperature is lowered to −78° C. and a solution of diphenyl-sulfonyloxaziridine (1.17 g, 4.5 mmoles) in 10 ml absolute tetrahydrofurane is added. After stirring for 30 minutes glacial acetic acid (257 μl, 4.5 mmoles) is added and the mixture is concentrated in vacuo and the remanecens is subjected to column chromatography using methylenechloride/ethylacetate (95/5) as eluent. The fractions containing the product is concentrated in vacuo yielding the title compound as a yellow oil.

1-(4-hydroxy-3-oxo-2,6,6-trimethyl-1-cyclohexen-1-yl)-3-methyl-5-benzenesulfonyl-1,3-pentadiene A solution of 1-(4-hydroxy-3-oxo-2,6,6-trimethyl-1-cyclo- hexen-1-yl)-3-methyl-3-trimethylsiloxy-1,4-pentadiene (200 mg, 0.62 mmol) in 1 ml glacial acetic acid is added benzenesulfinic acid, sodium salt (153 mg, 0.93 mmoles) and the mixture is stirred overnight at ambient temperature. The mixture is concentrated in vacuo and the remanecens is taken up in 10 ml diethylether and 10 ml 1M sodium hydroxide. The aqueous layer is separated and extracted twice with 10 ml diethylether. The combined ether phases are dried and concentrated in vacuo yielding the title compound as a slightly yellow oil.

We claim:

1. A compound having the formula

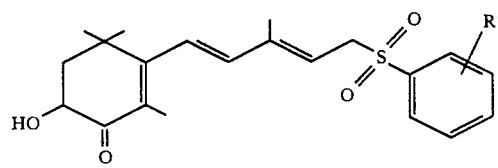

wherein R' is alkyl, alkoxy, No₂, NH₂ or halogen.

2. A method for the preparation of a compound having the formula

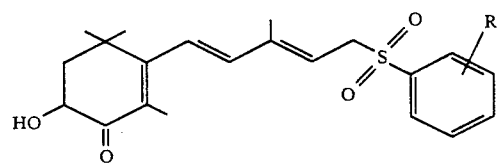

wherein R' is alkyl, alkoxy, NO₂, NH₂ or halogen, which method comprises the step of reacting a compound having the formula

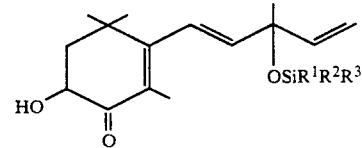

wherein $R^1$, $R^2$ and $R^3$ independently are $C_{1-6}$-alkyl which may be branched or phenyl with a compound having the formula

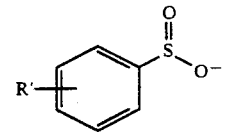

wherein R' is alkyl, alkoxy, NO₂, NH₂ or halogen.

* * * * *